United States Patent [19]

Hoelderich et al.

[11] Patent Number: 5,126,493
[45] Date of Patent: Jun. 30, 1992

[54] ALKOXYLATION OF ACTIVE HYDROGEN COMPOUNDS

[76] Inventors: Wolfgang Hoelderich, 18c Mannheimer Strasse, 6710 Frankenthal; Jochen Houben, 93 Benzstrasse, 6520 Worms; Gerhard Wolf, 31 Robert-Blum-Strasse, 6800 Mannheim, all of Fed. Rep. of Germany; Michael G. Kinnaird, 3612 Courtland Dr., Durham, N.C. 27707

[21] Appl. No.: 681,698

[22] Filed: Apr. 5, 1991

[51] Int. Cl.⁵ .............................................. C07C 41/03
[52] U.S. Cl. ................................... 568/616; 568/618; 568/620; 568/619; 568/45; 568/46; 568/606; 568/608; 568/619; 568/617; 568/675; 568/678; 554/64; 554/149; 554/227; 560/209; 560/240; 536/120; 564/475; 564/505

[58] Field of Search ............... 568/618, 616, 620, 619, 568/45, 46, 606, 608, 609, 617, 675, 678; 260/410.6; 560/209, 240; 536/120; 564/475, 505

[56] References Cited

U.S. PATENT DOCUMENTS 4,727,199 2/1988 King .................................. 568/618

Primary Examiner—Howard T. Mars

[57] ABSTRACT

Alkoxylates of active hydrogen compounds having a peaked molecular weight distribution are prepared by reacting the active hydrogen compound with an alkylene oxide of from 2 to 4 carbon atoms using iron oxides as alkoxylation catalysts.

6 Claims, No Drawings

ALKOXYLATION OF ACTIVE HYDROGEN COMPOUNDS

BACKGROUND OF THE INVENTION

1. Field of the Invention

The present invention relates to an improved process for alkoxylating active hydrogen compounds by reaction with an alkylene oxide of from 2 to 4 carbon atoms.

2. Description of the Related Art

Narrow distribution or "peaked" alkoxylates having a narrow molecular weight or homolog distribution are becoming increasingly important, since they have better application properties than the ordinary, broad distribution alkoxylates which are normally prepared using alkali metal hydroxides or alkoxides as catalysts. They find use in the main as surfactants in detergent and cosmetic compositions, but also in the paper and the textile fiber industries. There is therefore an urgent need for efficient processes for synthesizing such narrow distribution alkoxylates.

U.S. Pat. No. 3,957,922 (1) relates to a process for preparing alkoxylated products using aluminum or iron compounds as catalysts. The iron compounds mentioned are iron salts of customary mineral acids such as iron(III) chloride, iron(III) sulfate, iron(II) chloride, iron(II) sulfate, iron(II) nitrate and iron(III) phosphate, iron salts of fatty acids, iron powders, hydrates of iron(III) chloride and iron(II) chloride and sulfate and also commercial iron-coated catalyst materials.

EP-B-090,445 (2) relates to a process for polymerizing epoxides using double metal cyanide complexes as catalysts. These complexes may contain iron(III) and iron(II) atoms. It is also possible for water-soluble iron(III) salts to be present.

U.S. Pat. No. 4,727,199 (3) describes heterogeneous alkoxylation catalysts consisting of a metal oxide bonded to an anion. One of the metal oxides mentioned is iron oxide. The anion-bound metal oxide catalysts are amorphous or predominantly amorphous.

OBJECTS OF THE INVENTION

The narrow distribution alkoxylates prepared as described in references (1) to (3) are still in need of improvement as regards their homolog distribution and their application properties. It is an object of the present invention to provide a process for preparing alkoxylates having improved properties.

We have found that this object is achieved by a process for preparing alkoxylates of active hydrogen compounds by reacting the active hydrogen compounds with an alkylene oxide of from 2 to 4 carbon atoms, which comprises using iron oxides as alkoxylation catalysts.

DESCRIPTION OF THE PREFERRED EMBODIMENTS

The iron oxide used can be any known iron oxide. The most important iron oxides are iron(II) oxide of the formula FeO, iron(III) oxide of the formula $Fe_2O_3$ and iron (II,III) oxide of the formula $Fe_3O_4$. Particularly good results are obtained with iron(III) oxide, which occurs in the two modifications $\alpha$-$Fe_2O_3$ (hematite), and $\gamma$-$Fe_2O_3$ (meghemite). Preference is given to $\alpha$-$Fe_2O_3$ which has a corundum structure. The iron oxides used are in general polycrystalline.

The catalytic activity of iron oxides is crucially determined by their surface area. Brunauer-Emmett-Teller (BET) surface areas of below 100 $m^2/g$ give only inadequate results, in particular an excessively high level of unconverted active hydrogen starting compound. Values within the range from 120 $m^2/g$ to 135 $m^2/g$ give the best results. Iron oxides having a BET surface area of greater than 135 $m^2/g$ are virtually impossible or very difficult to prepare, so that this value must be deemed a reasonable upper limit.

The iron oxides described can be prepared in a conventional manner, for example iron(II) oxide may be prepared by heating iron(III) oxalate in the absence of air or iron(II) oxide by thermal dehydration of iron(III) hydroxide. A preferred method for preparing iron(III) oxide is the oxidation of iron pentacarbonyl by means of atmospheric oxygen at about 600° C.

The alkoxylation process, or oxyalkylation process as it is often called, according to the present invention is customarily carried out at 50°-230° C., preferably at 100°-180° C. Above 230° C. there is a distinct drop in catalyst activity, probably because the total surface area shrinks due to baking together of the particles. Particularly good results in respect of a sharply peaked homolog distribution are obtained at 140°-160° C.

The reaction is in general carried out under superatmospheric pressure, for example in an autoclave at 3-6 bar. The reaction is advantageously carried out without a solvent, but an inert solvent may be present. Under the conditions mentioned, the reaction normally takes 5-10 hours.

The alkoxylation catalyst, which is preferably composed of one but may also be composed of more than one iron oxide, is used in an amount of from 0.1 to 25% by weight, preferably from 0.5 to 15% by weight, based on the amount of active hydrogen compound. Especially preferred is an amount of from 2 to 10% by weight, in particular with respect to a low level of unconverted active hydrogen starting compound.

The active hydrogen compound used can be any compound which has one or more acidic hydrogen atoms capable of reaction with alkylene oxides. There may be mentioned here in particular alcohols, phenols, carbohydrates, carboxylic acids, carboxamides, amines and mercaptans, which fall within the general formula II

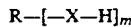

$$R-[-X-H]_m \qquad II$$

where R is a customary hydrocarbon radical which may contain hetero atoms and carry further functional groups, X is O, S, NH or NR, and m is 1, 2, 3, or more. Depending on m, R is monovalent, divalent or trivalent. Preference is given to monovalent and divalent radicals, especially the former.

Particular meanings of R are:

straight-chain or branched $C_1$-$C_{30}$-alkyl and $C_3$-$C_{30}$-alkenyl, which may each be interrupted by one or more nonadjacent oxygen atoms and may carry additional hydroxyl groups, e.g. methyl, ethyl, n-propyl, isopropyl, n-butyl, 2-ethylhexyl, n-octyl, isononyl, decyl, n-dodecyl, isotridecyl, myristyl, cetyl, stearyl, eicosyl, 2-propenyl, oleyl, linolyl, linolenyl, 2-methoxyethyl, 2-ethoxyethyl, 2-butyoxyethyl, 4-methoxybutyl, 4-(4'-methoxybutyloxy)-butyl, 2-hydroxyethyl or 4-hydroxybutyl; $C_1$-$C_{30}$-acyl, which may additionally carry hydroxyl groups, e.g. formyl, acetyl, propionyl, butyryl, valeryl, decanoyl, lauroyl, myristoyl, palmitoyl, stearoyl or lactyl;

monovalent carbohydrate radicals of mono- or disaccharides if X is O, e.g. of glucose, mannose, fructose, sucrose, lactose or maltose;

aryl having in total from 6 to 20 carbon atoms, which may additionally be substituted by $C_1$-$C_4$-alkyl, hydroxyl, $C_1$-$C_4$-alkoxy or amino, e.g. phenyl, tolyl, xylyl, hydroxyphenyl, methoxyphenyl, aminophenyl or naphthyl;

arylcarbonyl having in total from 7 to 21 carbon atoms, which may additionally be substituted by $C_1$-$C_4$-alkyl, hydroxyl, $C_1$-$C_4$-alkoxy or amino, e.g. benzoyl;

divalent radicals derived for example if X is O from diols, dihydroxy aromatics or bisphenols, such as 1,2-ethylene, 1,3-propylene, 1,4-butylene, phenylene or the radical of bisphenol A;

trivalent radicals derived for example if X is O from triols such as glycerol.

In a preferred embodiment, the active hydrogen compound II, is a $C_1$-$C_{30}$-alkanol or a $C_3$-$C_{30}$-alkenol, in particular a $C_8$-$C_{30}$-alkanol or -alkenol (a fatty alcohol).

The process according to the present invention produces from the active hydrogen compounds II alkoxylation products of the general formula I

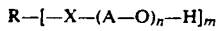

$$R-[-X-(A-O)_n-H]_m \quad I$$

where A is 1,2-alkylene of from 2 to 4 carbon atoms, preferably of 2 or 3 carbon atoms, and the degree of alkoxylation, n, is from 1 to 100, preferably from 1 to 20, in particular from 2 to 15. The narrowest homolog distribution of the alkoxylation products is obtained when n is from 3 to 10.

The alkylene oxide used is in particular propylene oxide or ethylene oxide, in particular the latter, but it is also possible to use a butylene oxide such as ethyloxirane, 1,2-dimethyloxirane or 1,1-dimethyloxirane.

The alkoxylates produced by the process according to the present invention have a sufficiently narrow molecular weight distribution; that is, the proportion of homologs having a low or high degree of alkoxylation is small. In general about 75%, advantageously about 85% or more, of the homologs are within a range of 5 alkylene oxide units.

Owing to the narrow molecular weight or homolog distribution, alkoxylates from the process according to the present invention which are used as surfactants in aqueous detergent formulations are sufficiently soluble and do not make the solutions undesirably viscous, two properties which are difficult to obtain at one and the same time from the customary alkoxylates having a broad molecular weight distribution.

Furthermore, the alkoxylates produced by the process according to the present invention contain only small residual concentrations of the active hydrogen starting compounds, for example fatty alcohols, which in many cases, if present in excessively high concentration, lead to odor problems in the alkoxylates and make it difficult to work up these products, for example by spray drying.

The use of iron oxides which are highly active as alkoxylation catalysts but otherwise inert has further advantages. The iron oxides used, being insoluble and having a certain particle size distribution, are easy to filter out of the liquid products or reaction mixtures. The products obtained are colorless and have a neutral pH. In principle, the removable iron oxides are regenerable and hence re-employable for further alkoxylations.

EXAMPLE 1

Preparation of n-dodecanol ethoxylate Having a Homolog Peak at 3 Mol of Ethylene Oxide 250 g (1.34 mol) of n-dodecanol and 12.5 g of α-iron-(III) oxide having a BET surface area of 135 m$^2$/g (corresponding to 5% by weight, based on n-dodecanol) were introduced into a 2-liter steel autoclave. The autoclave was flushed twice with nitrogen and then heated to 150° C. Ethylene oxide in an amount of 177 g (4.02 mol) was injected over the course of 4 hours during which the pressure did not exceed 6 bar. Thereafter the contents were stirred at 150° C. for 3 hours until the pressure was constant.

The product obtained was filtered while still hot. The filtrate was a colorless, clear liquid having neutral pH. FIG. 1 shows the homolog distribution of the alkoxylation product.

EXAMPLES 2a TO 2d

Effect of BET Surface Area of Catalyst

Example 1 was repeated, except that 250 g of n-dodecanol were reacted with 177 g of ethylene oxide in the presence of 5 g each time of α-iron(III) oxides (corresponding to 2% by weight, based on n-dodecanol) having different BET surface areas. Table 1 shows the residual level of unconverted n-dodecanol as a function of the BET surface area.

TABLE I

| Example | BET surface area [m$^2$/g] | Residual level of n-dodecanol [% by weight] |
|---|---|---|
| 2a* | 39 | 15.4 |
| 2b* | 90 | 21.7 |
| 2c | 112 | 11.1 |
| 2d | 135 | 6.9 |

*not according to the present invention

EXAMPLES 3a TO 3e

Effect of Catalyst Concentration

Example 1 is repeated, except that 250 g of n-dodecanol were reacted with 177 g of ethylene oxide in the presence of different amounts of α-iron(III) oxide having a BET surface area of 135 m$^2$/g. Table 2 shows the residual level of unconverted n-dodecanol as a function of the amount of catalyst.

TABLE 2

| Example | Amount of catalyst % by weight, based on n-dodecanol used] | Residual level of n-dodecanol [% by weight] |
|---|---|---|
| 3a | 0.5 | >10.0 |
| 3b | 2 | 6.9 |
| 3c | 5 | 1.9 |
| 3d | 10 | 3.0 |
| 3e | 15 | >3.0 |

EXAMPLE 4

Preparation of n-dodecanol ethoxylate Having a Homolog Peak at 5 Mol of Ethylene Oxide Example 1 was repeated, except that 250 g (1.34 mol) of n-dodecanol were reacted with 354 g (8.04 mol) of ethylene oxide in the presence of 5 g of α-iron(III) oxide having a BET surface area of 135 m$^2$/g (corresponding to 2% weight, based on n-dodecanol). Filtration left a colorless, viscous liquid. FIG. 2 shows the homolog distribution of the alkoxylation product.

EXAMPLES 5a TO 5d

Effect of Reaction Temperature

Example 4 was repeated, except that 250 g of n-dodecanol were reacted with 354 g of ethylene oxide in the presence of 5 g of α-iron(III) oxide having a BET surface area of 135 m²/g at various temperatures. Table 3 shows the maximum attainable level of the peak homolog in the product mixture, namely the reaction product with 5 mol of ethylene oxide, as a function of the reaction temperature.

TABLE 3

| Example | Reaction temperature [C.°] | Maximum level of reaction product with 5 mol of ethylene oxide [% by weight] |
|---|---|---|
| 5a | 100 | <20.0 |
| 5b | 125 | 20.7 |
| 5c | 150 | 23.0 |
| 5d | 180 | 19.8 |

We claim:

1. A process for preparing an alkoxylation product of an active hydrogen compound by reacting the active hydrogen compound with an alkylene oxide of from 2 to 4 carbon atoms, which comprises using a polycrystalline iron oxide as alkoxylation catalyst.

2. A process as claimed in claim 1, wherein the iron oxide used is iron(III) oxide.

3. A process as claimed in claim 1, wherein the iron oxide used has a BET surface area of from 100 m²/g to 135 m²/g.

4. A process as claimed in claim 1, wherein the iron oxide is used in an amount of from 0.1 to 50% by weight, based on the amount of active hydrogen compound.

5. A process as claimed in claim 1 for preparing an alkoxylation product of the general formula I $$R-[-X-(A-O)_n-H]_m \qquad I$$

where R is a hydrocarbon radical which may contain a hetero atom and carry a further functional group, X is O, S, NH or NR, A is 1,2-alkylene of from 2 to 4 carbon atoms, n is from 1 to 100, and m is 1, 2 or 3, by reacting the corresponding active hydrogen compound of the general formula II $$R-[-X-H]_m \qquad II$$

wherein m is 1, 2, or 3 with an alkylene oxide of from 2 to 4 carbon atoms.

6. A process as claimed in claim 5 for preparing an alkoxylation product I where R is $C_1$-$C_{30}$-alkyl or $C_3$-$C_{30}$-alkenyl, X is O, A is 1,2-alkylene of 2 or 3 carbon atoms, n is from 1 to 20, and m is 1.

* * * * *